(12) United States Patent
Bowen et al.

(10) Patent No.: US 7,793,892 B1
(45) Date of Patent: Sep. 14, 2010

(54) TUBE, WIRE AND CONDUIT HOLDER

(75) Inventors: Michael L. Bowen, Fort Worth, TX (US); George D. Reese, Keller, TX (US)

(73) Assignee: Prestige Ameritech Ltd., Fort Worth, TX (US)

( * ) Notice: Subject to any disclaimer, the term of this patent is extended or adjusted under 35 U.S.C. 154(b) by 242 days.

(21) Appl. No.: 12/033,307

(22) Filed: Feb. 19, 2008

(51) Int. Cl.
*F16L 3/00* (2006.01)
*A61M 5/32* (2006.01)

(52) U.S. Cl. .............. 248/49; 248/205.2; 604/174; 604/180; 604/179; 428/343; 24/306; 128/DIG. 26

(58) Field of Classification Search ............ 248/49, 248/51, 68.1, 205.2, 690; 211/85.13, 60.1, 211/70.4; 604/180, 174, 179; 128/DIG. 26; 24/306; 428/343
See application file for complete search history.

(56) References Cited

U.S. PATENT DOCUMENTS

| | | | |
|---|---|---|---|
| 3,881,474 A * | 5/1975 | Krzewinski | 128/852 |
| 4,074,397 A | 2/1978 | Rosin | |
| 4,336,806 A | 6/1982 | Eldridge, Jr. | |
| 4,417,710 A | 11/1983 | Adair | |
| 4,447,238 A | 5/1984 | Eldridge, Jr. | |
| 5,010,899 A | 4/1991 | Thompson | |
| 5,037,397 A | 8/1991 | Kalt et al. | |
| 5,147,322 A | 9/1992 | Bowen et al. | |
| 5,266,401 A * | 11/1993 | Tollini | 428/343 |
| 5,300,037 A * | 4/1994 | Delk et al. | 604/180 |
| 5,304,146 A | 4/1994 | Johnson et al. | |
| 5,397,639 A * | 3/1995 | Tollini | 428/343 |
| 5,468,231 A * | 11/1995 | Newman et al. | 604/180 |
| 5,707,703 A | 1/1998 | Rothrum et al. | |
| 5,778,889 A | 7/1998 | Jascomb | |
| 5,785,690 A | 7/1998 | Newman et al. | |
| 6,187,126 B1 | 2/2001 | Rothrum et al. | |
| 6,565,537 B2 * | 5/2003 | Tollini | 604/174 |
| 2006/0041233 A1 * | 2/2006 | Bowen | 604/180 |

* cited by examiner

*Primary Examiner*—Anita M King
(74) *Attorney, Agent, or Firm*—Geoffrey A. Mantooth (57) ABSTRACT

A holder or organizer has first and second strips releasably fastened together by coupling material such as by hook and loop material. The strips each have two ends, namely a bonding end and a free end. The two bonding ends are coupled together. The first strip has an adhesive on its outside. The second strip has a selvedge area adjacent an edge, which selvedge area lacks releasable coupling material. The selvedge area will not fasten to the first strip. A user can easily grip the selvedge area of the second strip and peel the second strip off of the first strip. A tongue extends in the direction of the bonding ends of the strips and works in conjunction with a non-tongue area of the upper strip to more securely hold an object in the holder.

25 Claims, 5 Drawing Sheets

TUBE, WIRE AND CONDUIT HOLDER

FIELD OF THE INVENTION

The present invention relates to apparatuses for holding tubes, wires, conduits and other devices in place, such as are found on medical drapes and other objects.

BACKGROUND OF THE INVENTION

Sterile drapes are used in surgical procedures to establish a sterile field. A drape is a sheet that covers some or all of the patient undergoing surgery. The drape has an aperture which is positioned over the area that is prepared for surgery. For example, in abdominal surgery, the drape aperture is positioned over the abdominal area of interest to the surgeon.

During the surgical procedure, sterile objects may be placed on the sterile drape; so placing an object maintains its sterility and allows the continued use of the object in the surgical procedure. For example, a suction tube may be used to suction fluids. If not in use, the tube is laid on the drape. If the suction tube falls or slides off of the drape and moves outside of the sterile field (such as falls in the floor), then the tube must be disposed of and a new sterile tube must be rigged for use.

Consequently, sterile drapes have evolved to be equipped with tube holders or organizers. A tube holder releasably holds the tube to the drape, thereby maintaining the tube on the drape and in the sterile field. Typically, a drape has several tube holders that are preattached to the drape.

There are a number of types of tube holders in the prior art. However, the marketplace prefers just one type because of its low cost. This prior art tube holder has two strips of a hook and loop fastener. The bottom strip is loop material and has adhesive. The bottom strip is adhered to the drape. The top strip is hook material. The strips are bonded together at one end, while the other ends are uncoupled and free. To secure a tube to the drape, the free end of the top strip is pulled up to release the top strip, the tube is placed on the lower loop material and the top strip is pressed back onto the loop material.

A problem with the prior art tube holder lies in the difficulty in separating the top strip from the bottom strip. The user has difficulty acquiring a grip on the top strip. The hook and loop strips have a low profile relative to the drape. It is difficult to grip the top strip free end with bare hands; the task is even more difficult with gloved hands as used in surgical procedures. Gloves are required to maintain the sterile field. The top strip, which is of hook material, is shorter than the bottom strip, but this does not ease the user's ability to acquire a grip on the top strip so as to pull it open.

Instead, drape manufacturers have developed a common practice of partially offsetting the top strip to the side of the bottom strip. However, because the tube holder is manufactured with the top and bottom strips aligned and not offset, the offsetting is accomplished by hand. This raises the cost of manufacture of the drape.

Another problem with the prior art tube holder is its low strength in securing or holding the tube in place. Once a tube is located inside of a holder and secured therein, the top strip is pressed on to the bottom strip. The top strip rolls over the tube leaving substantial empty space between the top and bottom strips, which empty space is located to the sides of the tube. Consequently, the tube can roll or slide along the bottom strip. If the tube is moved several times, such as being bumped or snagged, then the tube will work itself into prying the top strip off at the bottom strip. The tube will free itself.

SUMMARY OF THE INVENTION

The present invention provides a holder that comprises first and second strips. The first strip has an inside and an outside, with the outside having an adhesive. The first strip has a bonding end and a free end. The second strip is of a flexible material and has an inside and an outside. The second strip has a bonding end and a selvedge area. The first and second strips are coupled together at the respective bonding ends so that the inside of the first strip faces the inside of the second strip. Releasable coupling material comprising hook and loop material is located on the respective insides of the first and second strips to allow the first and second strips to refasten to each other. The selvedge area of the second strip is spaced from the bonding ends and located along an edge of the second strip. The second strip selvedge area will not couple to the first strip.

In accordance with one aspect of the present invention, the selvedge area comprises an area lacking hook and loop material.

In accordance with another aspect of the present invention, the selvedge area comprises a melted portion of the releasable coupling material.

In accordance with still another aspect of the present invention, the selvedge area is adjacent to a free end of the second strip.

In accordance with another aspect of the present invention, the first strip has a constant width for substantially most of its length from the first strip bonding end to the first strip free end. The second strip free end is narrower than the first strip width. The second strip free end comprises lateral cuts.

In accordance with still another aspect of the present invention, the second strip is shorter than the first strip, wherein the second strip free end is intermediate the first strip bonding end and free end when the first and second strips are fastened together.

In accordance with still another aspect of the present invention, the holder further comprises a tongue in the second strip and a non-tongue area on the second strip. The tongue has a free end and a coupling end. The tongue coupling end is coupled to the second strip. The tongue free end extends in the direction of the bonding ends. The non-tongue area is adjacent to the tongue. The tongue free end is capable of separating from the non-tongue area.

In accordance with another aspect of the present invention, the tongue is located between two non-tongue areas.

The present invention also provides a holder that comprises first and second strips. The first strip has an inside and an outside, with the outside having an adhesive. The first strip has a bonding end and a free end. The second strip is of flexible material and has an inside and an outside. The second strip has a bonding end and a free end. The first and second strips are coupled together at the respective bonding end so that the inside of the first strip faces the inside of the second strip. Releasable coupling material comprising hook and loop material is located on the respective insides of the first and second strips to allow the first and second strips to refasten to each other. A tongue is in the second strip and has a free end and a coupling end. The tongue free end extends in the direction of the bonding ends. The tongue coupling end is coupled to the second strip. A non-tongue area is on the second strip and is adjacent to the tongue. The tongue free end is capable of separating from the non-tongue area.

In accordance with another aspect of the present invention, the tongue is located between two non-tongue areas.

In accordance with another aspect of the present invention, the second strip has side edges. The tongue is lateral of the non-tongue area.

The present invention also provides a holder for an object that comprises first and second strips. The first strip has an inside and an outside, with the outside having an adhesive. The first strip has a bonding end and a free end. The second strip is of a flexible material and has an inside and an outside. The second strip has a bonding end and a free end. The first and second strips are coupled together at the respective bonding ends so that the inside of the first strip faces the inside of the second strip. Releasable coupling material comprising hook and loop material is located on the respective insides of the first and second strips to allow the first and second strips to refasten to each other. The second strip comprises a tongue, with the tongue having a free end that can be moved with respect to the remainder of the second strip. The second strip comprises an intermediate portion that is structured and arranged to extend across the object. The intermediate portion extends between the second strip bonding end and a junction on the second strip between the tongue and a non-tongue area. The object is capable of being located between the tongue and the non-tongue area.

The present invention also provides a drape for use in medical procedures. The drape comprises a sheet. A holder comprises first and second strips. The first strip has an inside and an outside, with the outside coupled to the sheet. The first strip has a bonding end and a free end. The second strip is of flexible material and has an inside and an outside. The second strip has a bonding end and a free end. The first and second strips are coupled together at their respective bonding ends so that the inside of the first strip faces the inside of the second strip. Releasable coupling material comprising hook and loop material is located on the respective insides of the first and second strips to allow the first and second strips to refasten to each other. The second strip free end has a selvedge area that does not fasten to the first strip, the selvedge area located along an edge of the second strip.

In accordance with another aspect of the present invention, the first strip has a constant width for substantially most of its length from the first strip bonding end to the first strip free end. The second strip free end is narrower than the first strip width. The second strip free end comprises lateral cuts. In accordance with another aspect of the present invention, the selvedge area comprises an area lacking coupling material.

In accordance with still another aspect of the present invention, the selvedge area comprises a melted portion of the releasable coupling material.

In accordance with another aspect of the present invention, the second strip comprises a tongue, with the tongue having a free end that can be moved with respect to the remainder of the second strip. The second strip comprises an intermediate portion that is structured and arranged to extend across the object. The intermediate portion extends between the second strip bonding end and a junction on the second strip between the tongue and a non-tongue area. The object is capable of being located between the tongue and the non-tongue area.

DESCRIPTION OF THE PREFERRED EMBODIMENT

Figure 1:
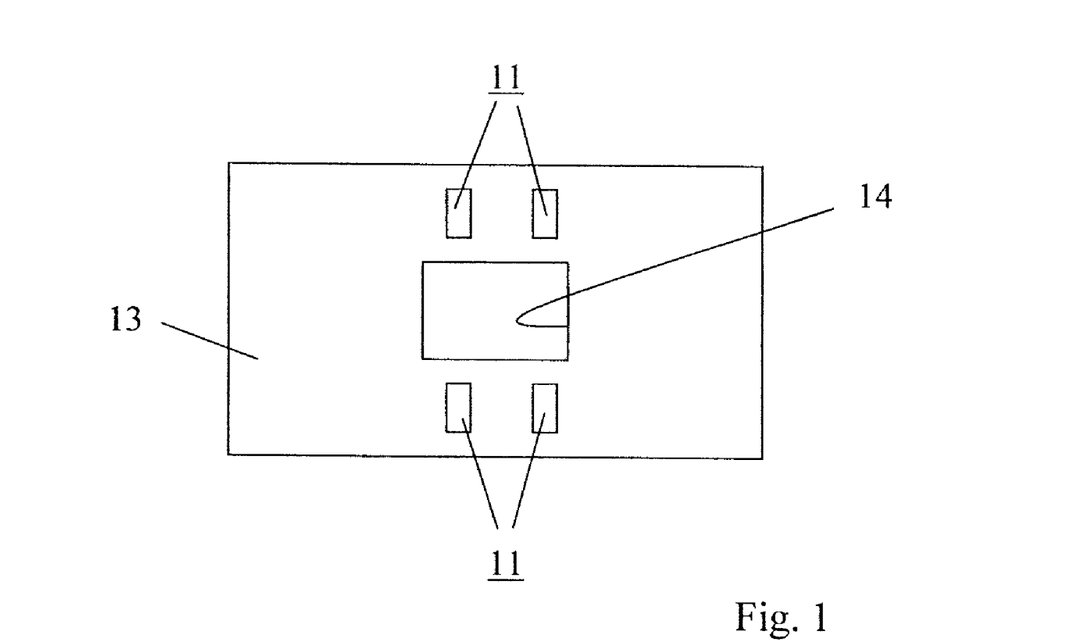
FIG. 1 is a plan view of a drape.

In FIG. 1, there is shown a drape 13 having a number of holders 11 thereon. The drape or sheet 13 is used in medical procedures, such as surgery. The holders 11 are used to secure objects, such as tubes, cables, wires, conduits, etc. to the drape 13.

The holder 11 (see FIG. 2) is easy to open by a human. To simplify the opening of the holder, the holder provides a selvedge area that is easy to grip and pull the holder apart.

Figure 2:
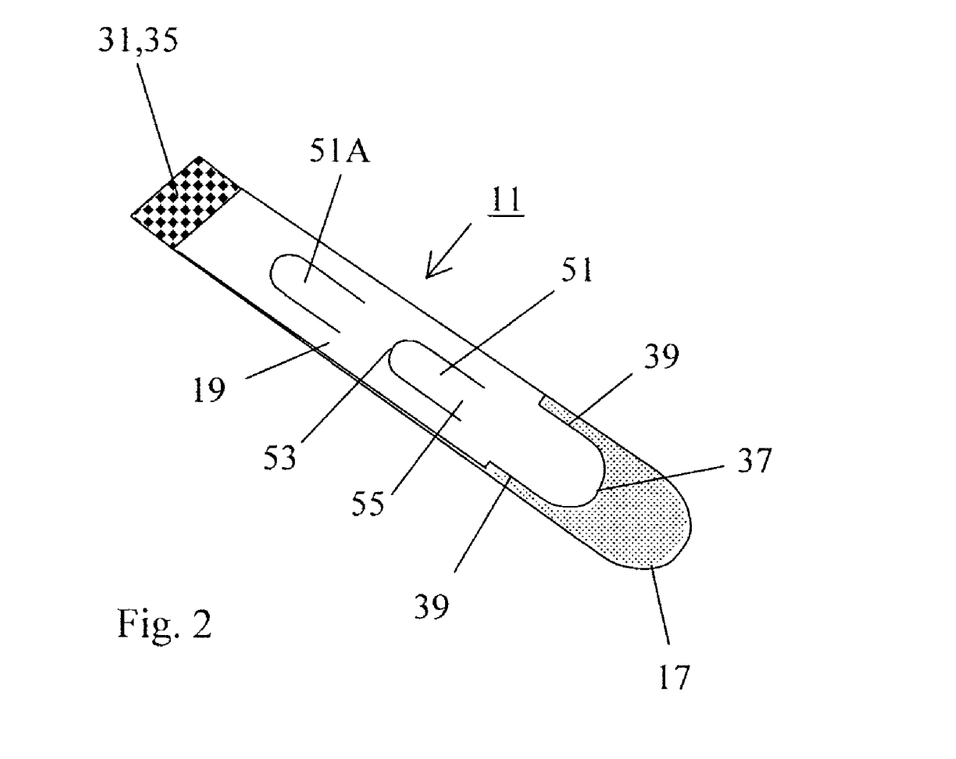
FIG. 2 is a view of the holder of the present invention, in accordance with a preferred embodiment.

Conversely, the holder more securely holds the tube or other object by way of a tongue. The tongue minimizes the tube pulling the holder pieces apart.

Although the holder is described herein in conjunction with a drape, the holder can be used in other applications such as on trays, equipment, lights, etc. Also, the holder can be used in non-surgical settings. For example, the tube holder can be adhered to a patient's hospital gown or clothes, or even to a patient's skin. Still other applications for the holder are outside the hospital or medical field. For example, a technician may use a holder to secure a wire bundle to a support, wall, etc.

Although the holder is described herein in conjunction with a tube, the holder can secure other objects such as wires, cables, instruments, etc.

The specifics of the drape 13 and holder 11 will now be described.

The drape or sheet 13 is, with the exception of the holders 11, conventional and commercially available. The drape can be of any size or configuration. Some drapes 13 are provided with apertures 14 to allow access to the patient. Some drapes have pouches for collecting fluid. The drape can be a surgical sheet or a non-surgical sheet, such as a bed sheet. The holder 11 can be used on any drape or sheet.

Figure 3:
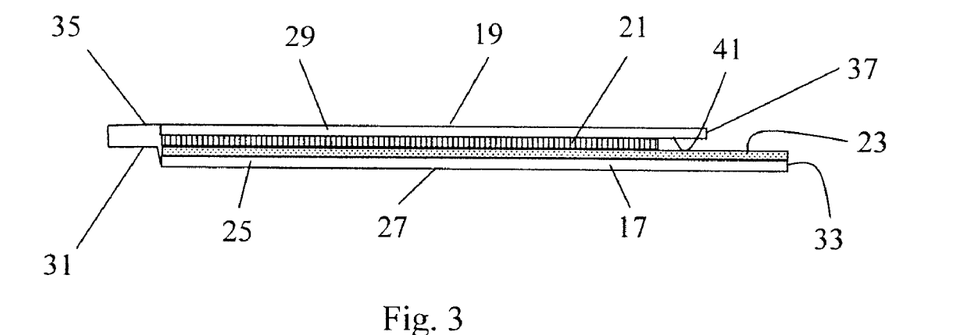
FIG. 3 is a side elevational view of the holder of FIG. 2, shown closed.
Figure 4:
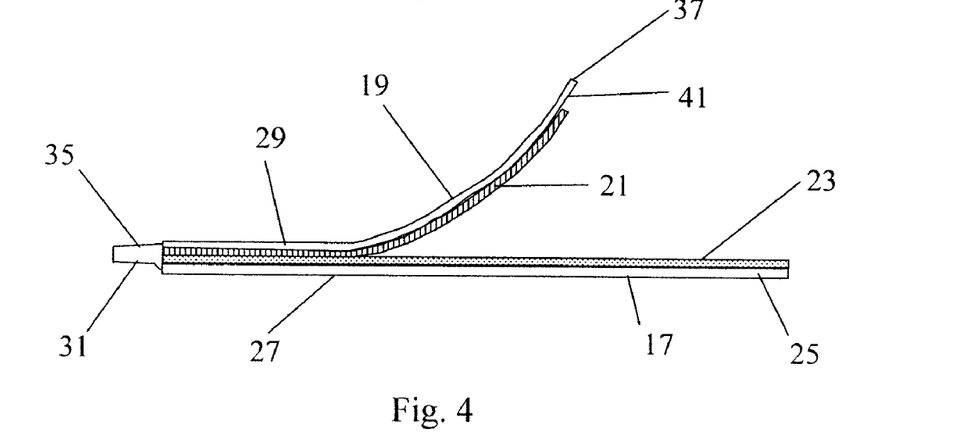
FIG. 4 is a side elevational view of the holder, shown opened.

Referring to FIGS. 2-4, the holder 11 has two strips, namely a lower strip 17 and an upper strip 19. (In FIGS. 3 and 4, the thickness of the strips is exaggerated for illustrative purposes.) The strips 17, 19 removably or releasably couple to each other by way of a hook and loop fastener. The hook and loop fastener comprises hook material 21 which is on one strip and loop material 23 which is on the other strip. In the preferred embodiment, the loop material 23 is on the lower strip 17, while the hook material 21 is on the upper strip 19. This is because the loop material 23 is softer and less likely to snag or tear a glove than the hook material 21. If this is of no concern, then the hook material could be on the bottom strip, with the hoop material on the top strip.

The lower strip 17 has a backing layer 25 and loop material 23 on the backing layer. The loop material 23 forms an inside of the lower strip 17 while the backing material forms the outside. A layer of adhesive 27 is on the outside, along the backing layer 25. The adhesive 27 allows the lower strip 17 to be coupled to the drape 13. As discussed above, the holder can be used in other, non-drape, applications. The adhesive 27 allows the holder to couple to the object which will support the holder. A protective, peelable liner (not shown) is applied to the adhesive 27 to prevent inadvertent sticking or coupling of the holder before installation onto a drape.

The upper strip 19 has a backing layer 29 and hook material 21 on the backing layer. The hook material 21 forms an inside of the upper strip 19 while the backing layer 29 forms the outside.

The lower strip 17 has ends, namely a bonding end 31 and a free end 33. Likewise, the upper strip 19 has a bonding end 35 and a free end 37. The two strips 17, 19 are permanently coupled together at their respective bonding ends 31, 35. This is accomplished by ultrasonic bonding, by heat and pressure or by adhesive. The two insides with the hook and loop material 21, 23 face each other. In the preferred embodiment, the upper strip 19 is shorter than the lower strip 17.

Figure 5:
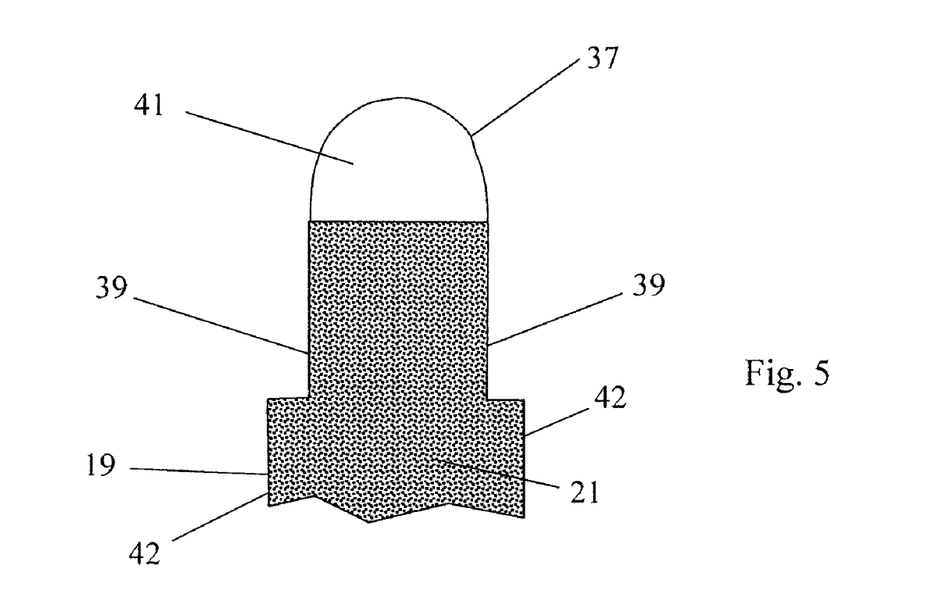
FIG. 5 is a plan view of the inside of the free end of the upper strip.

In order to make the upper strip 19 easier for a human to pull off of the lower strip 17, the upper strip is modified. The upper strip 19 is provided with a selvedge portion or area on the inside that is adjacent to an edge and is free of any hook or loop material. Referring to FIG. 5, the selvedge portion or area 41 of the upper strip 19 lacks any effective hook or loop material. In the embodiment shown in FIG. 5, the selvedge area 41 is located at the free end 37 of the upper strip. Consequently, the free end 37 of the upper strip 19 does not couple or stick to the lower strip 17.

The selvedge area 41 can be made in several ways. In one embodiment, the selvedge area 41 is made during the manufacture of the upper strip. During the manufacture, the hooks are limited to the hook, or non-selvedge, area of the upper strips. As will be discussed further below, the upper strip is cut from a web of hook material. In the prior art, this web has a selvedge edge of about 1/16 inch wide. The selvedge edge exists in prior art webs of hook material because the hooks cannot be made at the edge. Even though in the prior art, webs of hook material have a very thin selvedge edge, prior art upper strips are cut away from this selvedge edge. The prior art upper strips have no selvedge edge, at least at or near the free end.

In the present invention, the upper strip is cut from the web so as to create a selvedge area at or near the free end. The selvedge edge on the web of hook material is about 1/4-1/2 inches, extending from the edge inward. The selvedge area 41 is large enough to allow a human to grab the selvedge area and lift the upper strip off of the lower strip. The selvedge on the web material lacks hook and loop material. Instead, the selvedge edge is made of the backing layer 29.

Another way to make the selvedge area 41 is to mutilate the coupling, or hook or loop, material. For example, the coupling material can be melted. This is discussed in more detail below. Alternatively, the coupling material can be cut off of the backing layer. For example, the hooks can be cut or shaved off of the backing layer. As another example, the hooks can be compressed or pounded so as to become inoperable in coupling to the loop material. Still another way to make the selvedge area is to cover or block the coupling material. For example, if there is hook material on the backing, then loop material is pressed into place at the selvedge area. This loop material is separate from the loop material on the lower strip and may have its own backing layer. The loop material prevents the hook material in the selvedge area from coupling to the lower strip.

Figures 5A, 5B, 5C:
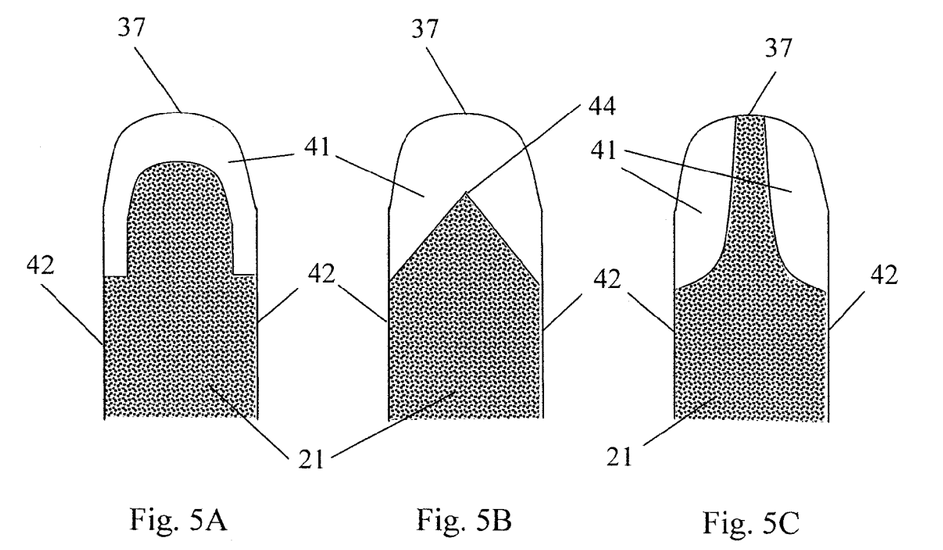
FIGS. 5A, 5B and 5C are plan views of the inside of the upper strip, showing alternative embodiments.

In the preferred embodiment, the selvedge area 41 is approximately shaped like a half circle, as can be seen in FIG. 5. The selvedge area 41 can be other shapes such as a crescent, as shown in FIG. 5A, where the selvedge area 41 extends from the free end 37 along the side edges 42 of the upper strip. Another shape of the selvedge area is illustrated in FIG. 5B, where the loop material 21 has an apex 44. The width of the selvedge area 41 from the inside edge 42 of the upper strip to the loop material 21 is greater than in FIG. 5A, at least near the free end 37. FIG. 5C shows another embodiment where there are two disconnected selvedge areas 41 extending along the side edges 42 for a distance. In FIG. 5C, the selvedge areas 41 are separated by the hook material 21.

In all these embodiments, the selvedge area or areas 41 are located along an edge of the upper strip to enable a human to separate the upper strip from the lower strip, as will be described below.

In addition, the free end 37 has lateral cuts 39 (see FIG. 5) along the sides 42 that narrow the width of the upper strip relative to the lower strip. The lateral cuts 39 make it easier for a user to see the upper strip free end 37. The lateral cuts extend from the free end 37 toward the bonding end 35. The upper strip 19 can be provided with (FIG. 5) or without (FIGS. 5A-5C) the lateral cuts 39.

In order to more securely hold the tube or other object inside of the holder and minimize accidental release, the holder is provided with one or more tongues.

Figure 6:
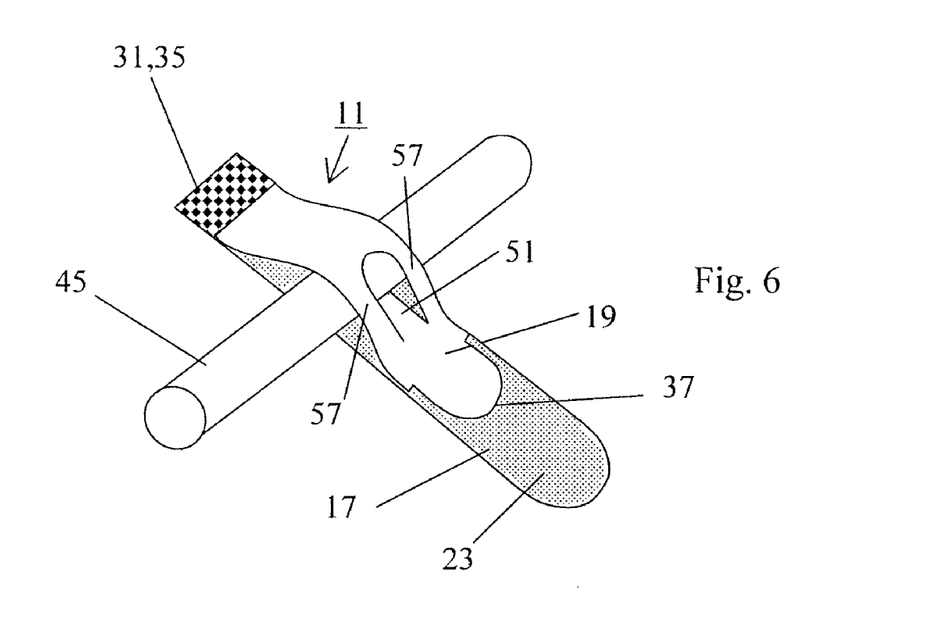
FIG. 6 is a view of the holder holding a tube.

The upper strip 19 has one or more tongues 51, 51A as shown in FIG. 2. The tongues are formed by a die cut. Each tongue extends in the direction of the length (from end 35 to end 37) of the strip 19. Each tongue has a free end 53 and a joined end 55. As shown in FIG. 6, the tongue free end 53 can separate from the remainder of the upper strip 19. The tongue free end 53 extends in the direction away from the upper strip free end 37. The tongue is coupled to or joined to the remainder of the upper strip at the joined end 55. The inside of the tongue has hook or loop material.

Figures 8A, 8B:
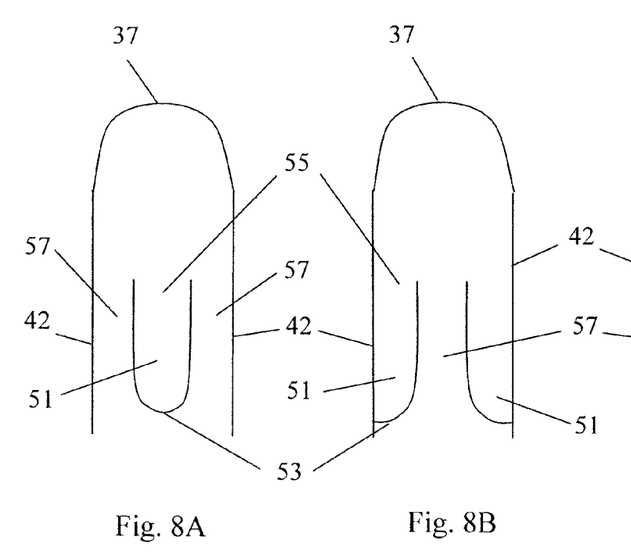
FIGS. 8A, 8B and 8C are plan views of the outside of the upper strip, showing various embodiments of tongues.
Figure 8C:
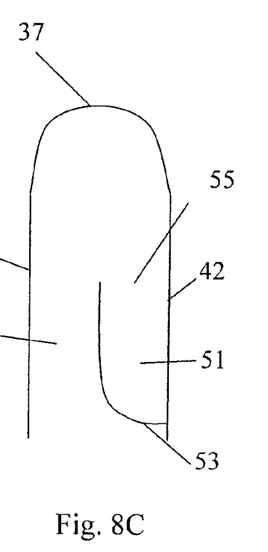

FIGS. 8A, 8B and 8C illustrate embodiments of tongues 51. FIG. 8A shows the tongue 51 as previously shown in FIG. 2. The tongue is centered between the side edges 42 of the upper strip. There are non-tongue areas 57 located between the tongue 51 and the side edges. FIG. 8B shows a center non-tongue area 57 with two lateral tongues 51. The two tongues 51 extend along the side edges 42. FIG. 8C shows a tongue 51 extending along one side edge 42, with a non-tongue area 57 extending along the other side edge 42.

To make a holder, a web of hook material 21 with backing 29 and a web of loop material 23 with backing 25 are used. The loop material 23 web has adhesive 27 with a paper liner. The manufacturing is automated so as to reduce the cost. The free ends 33, 37 are cut to shape and the tongue or tongues 51 are formed. The two webs are brought together so as to fasten the hook and loop material together. The two webs are bonded together at the bonding ends 31, 35. After bonding, the individual holders 11 are cut from the webs.

The web of hook material has two lateral edges. At least one edge has a selvedge edge of some width. In the preferred embodiment, the width of the selvedge edge is about 1/2 inch. The selvedge edge has a backing layer 29, but no hook material. As the upper strip is cut from the web, the selvedge area 41 is taken from the selvedge edge. Such a process will produce a selvedge area 41 such as is shown in FIG. 5.

Another way to make the selvedge area 41 is by melting the coupling material in the upper strip. Before the webs are brought together, the free ends 37 of the upper strips 19 are passed through a heating unit to melt the hook material and form the melted area 41. The heating unit can use ultrasonic energy or heat to melt the hook material. The melting causes the hooks to flatten or bond to the backing layer 29 so as to form the selvedge area 41 on the inside of the upper strip 19 that has no hook material. The free end 37 is thus unable to couple to the lower strip 17.

Once assembled, the holder 11 can be applied to a drape 13. The paper liner is peeled off from the adhesive 27 on the lower strip, and the lower strip 17 is pressed onto the drape 13 at the desired location.

Figure 7:
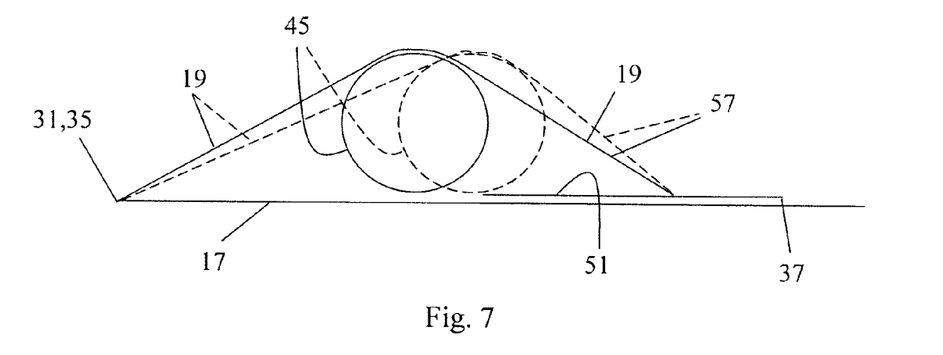
FIG. 7 schematically illustrates how a holder equipped with a tongue operates to secure a tube.

To use the holder 11, the user, who wears gloves, is able to easily grip the free end 37 of the upper strip 19. The user lifts the selvedge area 41 up off of the lower strip 17 and provides some separation from the lower strip 17. The user grips the free end 37. Because the free end of the upper strip is not coupled to the lower strip, this is a simple task for the user. Alternatively, the user can grip a side edge 42 of the upper strip. The user then pulls the upper strip 19 from the lower strip 17 as shown in FIG. 4. A tube 45 is laid onto the lower strip near the bonding ends 31, 35, as shown in FIG. 6. The tongue 51 is pushed in toward the lower strip 17. The tongue, which has hook material thereon, is pressed against the lower strip, followed by pressing the remainder of the upper strip free end to the lower strip. As shown in FIGS. 6 and 7, the upper strip 19 rolls over or extends over the tube 45. This leaves some room or "play" for the tube to move around in. The tube can move along the lower strip 17 in a side to side direction (referring to the orientation shown in FIG. 7). As the tube moves in the direction of the upper strip free end 37, it wedges between the upper and lower strips and has a tendency to pull the upper strip 19 off of the lower strip 17. However, the tongue 51 resists this pulling apart of the upper and lower strips 17, 19. The tongue 51 creates or increases the shear strength of the coupling between the upper and lower strips. Pull strength and shear strength are terms used by the hook and loop industry and the adhesive industry. Pull strength is resistance to a force that is normal to the strip. Shear strength is resistance to a force that is parallel to the strip. In a hook and loop fastener, pull strength is much less than shear strength.

Thus, the tongue 51 increases the coupling strength between the upper and lower strips. The tube can no longer simply pull the strips apart and instead must shear the strips apart.

In addition, the tongue 51 serves as an anchor, further increasing the coupling strength. As the tube (shown in dashed lines in FIG. 7) moves even closer to the free end 37 of the upper strip, it will contact the tongue 51. The tube is now located between two parts of the upper strip, namely the tongue 51 and the non-tongue area 57. The tube 45 presses the tongue 51 on to the lower strip 17. The tube is unable to pull the tongue 51 off of the lower strip.

To remove the tube, the upper strip 19 is pulled off of the lower strip 17 as described above, namely the user lifts the selvedge area 41 off the lower strip and grips the free end 37 or edge 42 that is adjacent to the selvedge area 41. The upper strip is then pulled off of the lower strip. If the tube is between the tongue 51 and the non-tongue area 57, the tongue will cause the tube to move or roll toward the bonding ends 31, 35 a sufficient distance to allow the tongue to be pulled off of the lower strip. Once the upper and lower strips are separated, the tube can be removed.

The placement and length of the tongue depends on the diameter and shape of the tube 45 or the object to be secured. As shown in FIG. 2, two tongues are provided. One tongue, 51, closer to the free end 37, is for relatively large tubes or objects. The other tongue, 51A, is closer to the bonding ends 31, 35, and is for relatively smaller tubes or objects. The tongue 51A can be shorter than the tongue 51.

The selvedge area 41 allows a human to more easily grip a piece of the upper strip in order to open the holder. Once the holder is closed around an object such as a tube, the tongue increases the strength of the holder and more securely holds the object inside of the holder. The tongue prevents or minimizes accidental release of the object.

Although the holder has been described herein as having both a selvedge area (or areas) 41 for ease of gripping the upper strip, and a tongue (or tongues) 51 for more securely holding an object inside of the holder, the holder need not have both of these aspects and can only have one aspect. For example, the holder can be provided with a selvedge area 41 and without a tongue. Alternatively, the holder can be provided with a tongue, but without a selvedge area 41.

The foregoing disclosure and showings made in the drawings are merely illustrative of the principles of this invention and are not to be interpreted in a limiting sense.

The invention claimed is:

1. A holder, comprising:
   a) a first strip having an inside and an outside, the outside having an adhesive, the first strip having a bonding end and a free end;
   b) a second strip of flexible material having an inside and an outside, the second strip having a bonding end and a selvedge area;
   c) the first and second strips coupled together at the respective bonding ends so that the inside of the first strip faces the inside of the second strip;
   d) releasable coupling material comprising hook and loop material on the respective insides of the first and second strips to allow the first and second strips to refasten to each other;
   e) the selvedge area of the second strip spaced from the bonding ends and located along an edge of the second strip, wherein the second strip selvedge area will not couple to the first strip;
   f) a tongue in the second strip, the tongue having a free end and a coupling end, the tongue free end extending in the direction of the bonding ends, the tongue coupling end coupled to the second strip;
   g) a non-tongue area in the second strip that is adjacent to the tongue, the tongue free end capable of separating from the non-tongue area.

2. The holder of claim 1, wherein the selvedge area comprises an area lacking hook and loop material.

3. The holder of claim 1, wherein the selvedge area comprises a melted portion of the releasable coupling material.

4. The holder of claim 1 wherein:
   a) the second strip comprises a free end;
   b) the selvedge area is adjacent to the free end.

5. The holder of claim 4 wherein the first strip has a constant width for substantially most of its length from the first strip bonding end to the first strip free end, the second strip free end being narrower than the first strip width, the second strip free end comprises lateral cuts.

6. The holder of claim 1 wherein the tongue is located between two non-tongue areas.

7. A holder, comprising:
   a) a first strip having an inside and an outside, the outside having an adhesive, the first strip having a bonding end and a free end;
   b) a second strip of flexible material having an inside and an outside, the second strip having a bonding end and a selvedge area;
   c) the first and second strips coupled together at the respective bonding ends so that the inside of the first strip faces the inside of the second strip;
   d) releasable coupling material comprising hook and loop material on the respective insides of the first and second strips to allow the first and second strips to refasten to each other;

e) the selvedge area of the second strip spaced from the bonding ends and located along an edge of the second strip, wherein the second strip selvedge area will not couple to the first strip;

f) the second strip is shorter than the first strip, with the second strip free end intermediate the first strip bonding end and free end when the first and second strips are fastened together.

8. A holder, comprising:

a) a first strip having an inside and an outside, the outside having an adhesive, the first strip having a bonding end and a free end;

b) a second strip of flexible material having an inside and an outside, the second strip having a bonding end and a free end;

c) the first and second strips coupled together at the respective bonding ends so that the inside of the first strip faces the inside of the second strip;

d) releasable coupling material comprising hook and loop material on the respective insides of the first and second strips to allow the first and second strips to refasten to each other;

e) a tongue in the second strip, the tongue having a free end and a coupling end, the tongue free end extending in the direction of the bonding ends, the tongue coupling end coupled to the second strip;

a non-tongue area in the second strip that is adjacent to the tongue, the tongue free end capable of separating from the non-tongue area.

9. The holder of claim 8 wherein the tongue is located between two non-tongue areas.

10. The holder of claim 8 wherein the second strip further comprises side edges, the tongue located lateral of the non-tongue area.

11. A holder for securing an object, comprising:

a) a first strip having an inside and an outside, the outside having an adhesive, the first strip having a bonding end and a free end;

b) a second strip of flexible material having an inside and an outside, the second strip having a bonding end and a free end;

c) the first and second strips coupled together at the respective bonding ends so that the inside of the first strip faces the inside of the second strip;

d) releasable coupling material comprising hook and loop material on the respective insides of the first and second strips to allow the first and second strips to refasten to each other;

e) the second strip comprising a tongue, the tongue having a free end that can be moved with respect to the remainder of the second strip;

f) the second strip comprises an intermediate portion structured and arranged to extend across the object, the intermediate portion extending between the second strip bonding end and a junction on the second strip between the tongue and a non-tongue area, the object capable of being located between the tongue and non-tongue area.

12. A drape for use in medical procedures, comprising:

a) a sheet;

b) a holder comprising first and second strips;

c) the first strip having an inside and an outside, the outside coupled to the sheet, the first strip having a bonding end and a free end;

d) the second strip is of flexible material and has an inside and an outside, the second strip having a bonding end and a free end;

e) the first and second strips coupled together at the respective bonding ends so that the inside of the first strip faces the inside of the second strip;

f) releasable coupling material comprising hook and loop material on the respective insides of the first and second strips to allow the first and second strips to refasten to each other;

g) the second strip free end having a selvedge area that does not fasten to the first strip, the selvedge area located along an edge of the second strip;

h) the second strip comprising a tongue, the tongue having a free end that can be moved with respect to the remainder of the second strip;

i) the second strip comprises an intermediate portion structured and arranged to extend across the object, the intermediate portion extending between the second strip bonding end and a junction on the second strip between the tongue and a non-tongue area, the object capable of being located between the tongue and non-tongue area.

13. The drape of claim 12 wherein the first strip has a constant width for substantially most of its length from the first strip bonding end to the first strip free end, the second strip free end being narrower than the first strip width, the second strip free end comprises lateral cuts.

14. The drape of claim 12, wherein the selvedge area comprises an area lacking hook and loop material.

15. The drape of claim 12, wherein the selvedge area comprises a melted portion of the releasable coupling material.

16. A holder for securing an object, comprising:

a) a first strip having an inside and an outside, the outside having an adhesive, the first strip having a bonding end and a free end;

b) a second strip of flexible material having an inside and an outside, the second strip having a bonding end and a free end;

c) the first and second strips coupled together at the respective bonding ends so that the inside of the first strip faces the inside of the second strip;

d) releasable coupling material on the respective insides of the first and second strips;

e) the second strip comprising a tongue, the tongue having a free end that can be moved with respect to the remainder of the second strip;

f) the second strip comprises an intermediate portion structured and arranged to extend across the object, the intermediate portion extending between the second strip bonding end and a junction on the second strip between the tongue and a non-tongue area, the object capable of being located between the tongue and non-tongue area.

17. The holder of claim 16, wherein the tongue is located between two non-tongue areas.

18. The holder of claim 16 wherein the second strip further comprises side edges, the tongue located lateral of the non-tongue area.

19. The holder of claim 16, further comprising a selvedge area on the second strip, the selvedge area spaced from the bonding ends, the selvedge area not coupling to the first strip.

20. A holder, comprising:

a) a first strip having an inside and an outside, the outside having an adhesive, the first strip having a bonding end and a free end;

b) a second strip of flexible material having an inside and an outside, the second strip having a bonding end and a free end;

c) the first and second strips coupled together at the respective bonding ends so that the inside of the first strip faces the inside of the second strip;

d) releasable coupling material on the respective insides of the first and second strips;
e) a tongue in the second strip, the tongue having a free end and a coupling end, the tongue free end extending in the direction of the bonding ends, the tongue coupling end coupled to the second strip;
f) a non-tongue area in the second strip that is adjacent to the tongue, the tongue free end capable of separating from the non-tongue area.

21. The holder of claim 20 wherein the tongue is located between two non-tongue areas.

22. The holder of claim 20 wherein the second strip further comprises side edges, the tongue located lateral of the non-tongue area.

23. A drape for use in medical procedures, comprising:
a) a sheet;
b) a holder comprising first and second strips;
c) the first strip having an inside and an outside, the outside coupled to the sheet, the first strip having a bonding end and a free end;
d) the second strip is of flexible material and has an inside and an outside, the second strip having a bonding end and a free end;
e) the first and second strips coupled together at the respective bonding ends so that the inside of the first strip faces the inside of the second strip;
f) releasable coupling material on the respective insides of the first and second strips;
g) a tongue in the second strip, the tongue having a free end and a coupling end, the tongue free end extending in the direction of the bonding ends, the tongue coupling end coupled to the second strip;
h) a non-tongue area in the second strip that is adjacent to the tongue, the tongue free end capable of separating from the non-tongue area.

24. The drape of claim 23, further comprising a selvedge area on the second strip, the selvedge area spaced from the bonding ends, the selvedge area not coupling to the first strip.

25. A holder, comprising:
a) a first strip having an inside and an outside, the outside having an adhesive, the first strip having a bonding end and a free end;
b) a second strip of flexible material having an inside and an outside, the second strip having a bonding end and a selvedge area;
c) the first and second strips coupled together at the respective bonding ends so that the inside of the first strip faces the inside of the second strip;
d) releasable coupling material on the respective insides of the first and second strips;
e) the selvedge area of the second strip spaced from the bonding ends and located along an edge of the second strip, wherein the second strip selvedge area will not couple to the first strip;
f) the second strip is shorter than the first strip, with the second strip free end intermediate the first strip bonding end and free end when the first and second strips are fastened together.

* * * * *